United States Patent
Muni et al.

(10) Patent No.: US 10,034,682 B2
(45) Date of Patent: *Jul. 31, 2018

(54) DEVICES, SYSTEMS AND METHODS USEABLE FOR TREATING FRONTAL SINUSITIS

(71) Applicant: Acclarent, Inc., Irvine, CA (US)

(72) Inventors: Ketan P. Muni, San Jose, CA (US); Carlos F. Fernandez, High Springs, FL (US); Joshua Makower, Los Altos, CA (US); John Y. Chang, Los Altos, CA (US); William M. Facteau, Atherton, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/465,978

(22) Filed: Mar. 22, 2017

(65) Prior Publication Data

US 2017/0238954 A1 Aug. 24, 2017

Related U.S. Application Data

(63) Continuation of application No. 14/515,687, filed on Oct. 16, 2014, now Pat. No. 9,610,428, which is a
(Continued)

(51) Int. Cl.
*A61M 29/00* (2006.01)
*A61B 17/24* (2006.01)
(Continued)

(52) U.S. Cl.
CPC .............. *A61B 17/24* (2013.01); *A61B 18/12* (2013.01); *A61M 25/0041* (2013.01);
(Continued)

(58) Field of Classification Search
CPC .... A61M 2029/025; A61M 2210/0681; A61M 25/0041; A61M 29/02
(Continued)

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CA | 2013323 | 9/1990 |
| CH | 668188 | 12/1988 |

(Continued)

OTHER PUBLICATIONS

Friedman, M., M.D., et al. 'Frontal Sinus Surgery: Endoscopic Technique' Operative Techniques in Otolaryngology—Head and Neck Surgery. vol. 12, No. 2 (Jun. 2001) pp. 60-65.
(Continued)

*Primary Examiner* — Kevin C Sirmons
*Assistant Examiner* — Deanna K Hall
(74) *Attorney, Agent, or Firm* — Frost Brown Todd LLC

(57) ABSTRACT

Devices, systems and methods wherein a dilator, such as a balloon or other expandable member, is positionable within the frontal sinus ostium and adjacent frontal recess and useable to dilate the frontal sinus ostium and substantially all of the frontal sinus recess without requiring repositioning and repeated re-expansion of the dilator. One balloon catheter device of the invention comprises a catheter body that is less than about 50 cm in length (and in some embodiments less than 25 cm in length and a semi-compliant or non-compliant balloon on the catheter body. The balloon may have a working length of about 12 mm to about 30 mm and a width at its widest point when fully inflated of about 2 mm to about 7 mm. Such balloon may be constructed to with-
(Continued)

stand inflation pressures of about 12 atmospheres. In some embodiments, the dilator is advanced through or over a guide (e.g., guidewire or guide catheter) that has a preformed shape.

20 Claims, 4 Drawing Sheets

Related U.S. Application Data continuation of application No. 11/355,512, filed on Feb. 16, 2006, now Pat. No. 8,894,614, which is a continuation-in-part of application No. 11/150,847, filed on Jun. 10, 2005, now Pat. No. 7,803,150, which is a continuation-in-part of application No. 10/944,270, filed on Sep. 17, 2004, now abandoned, which is a continuation-in-part of application No. 10/829,917, filed on Apr. 21, 2004, now Pat. No. 7,654,997.

(51) Int. Cl.
  *A61M 29/02* (2006.01)
  *A61M 25/09* (2006.01)
  *A61M 25/00* (2006.01)
  *A61M 25/01* (2006.01)
  *A61M 25/10* (2013.01)
  *A61M 31/00* (2006.01)
  *A61B 18/12* (2006.01)
  *A61B 17/22* (2006.01)
  *A61B 18/00* (2006.01)

(52) U.S. Cl.
  CPC ........ *A61M 25/0108* (2013.01); *A61M 25/09* (2013.01); *A61M 25/10* (2013.01); *A61M 29/02* (2013.01); *A61M 31/005* (2013.01); *A61B 2017/22061* (2013.01); *A61B 2018/00577* (2013.01); *A61B 2018/00601* (2013.01); *A61M 2025/1086* (2013.01); *A61M 2029/025* (2013.01); *A61M 2210/0618* (2013.01); *A61M 2210/0681* (2013.01)

(58) Field of Classification Search
  USPC .............................................. 604/96.01, 104
  See application file for complete search history.

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bezark |
| 3,037,286 A | 6/1962 | Bower |
| 3,173,418 A | 3/1965 | Baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,477,438 A | 11/1969 | Allen |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,802,096 A | 4/1974 | Matern |
| 3,804,081 A | 4/1974 | Kinoshita |
| 3,800,788 A | 7/1974 | White |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,445,892 A | 5/1984 | Hussein et al. |
| 4,450,150 A | 5/1984 | Sidman |
| 4,459,977 A | 7/1984 | Pizon et al. |
| 4,464,175 A | 8/1984 | Altman et al. |
| 4,467,790 A | 8/1984 | Schiff |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |

(56) References Cited

U.S. PATENT DOCUMENTS

| | | |
|---|---|---|
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,686,965 A | 8/1987 | Bonnet et al. |
| 4,691,948 A | 9/1987 | Austin, Jr. et al. |
| 4,696,544 A | 9/1987 | Costella |
| 4,700,694 A | 10/1987 | Shishido |
| 4,705,801 A | 11/1987 | Martin et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zenter et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,986,810 A | 1/1991 | Semrad |
| 4,991,588 A | 2/1991 | Pflueger et al. |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,084,010 A | 1/1992 | Plaia et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,090,959 A | 2/1992 | Samson et al. |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,201,908 A | 4/1993 | Jones |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deneiga |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,314,443 A | 5/1994 | Rudnick |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |

(56) References Cited

U.S. PATENT DOCUMENTS

| | | |
|---|---|---|
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,370,640 A | 12/1994 | Kolff |
| 5,372,138 A | 12/1994 | Crowley et al. |
| 5,372,584 A | 12/1994 | Zink et al. |
| D355,031 S | 1/1995 | Yoshikawa |
| 5,378,234 A | 1/1995 | Hammerslag et al. |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,309 A | 12/1995 | Sweezer et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,653,690 A | 8/1997 | Booth et al. |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,752,513 A | 5/1998 | Acker et al. |
| 5,752,971 A | 5/1998 | Rosenbluth et al. |
| 5,762,604 A | 6/1998 | Kieturakis |
| 5,766,158 A | 6/1998 | Opolski |
| 5,769,821 A | 6/1998 | Abrahamson et al. |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,827,323 A | 10/1998 | Klieman et al. |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |

(56) References Cited

U.S. PATENT DOCUMENTS

| | | |
|---|---|---|
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | MacKenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,102,891 A | 8/2000 | van Erp et al. |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,402 A | 11/2000 | Munoz |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hedge et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,264,087 B1 | 7/2001 | Whitman |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 9/2001 | Powell et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garribotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,488,653 B1 | 12/2002 | Lombardo |
| 6,491,940 B1 | 12/2002 | Levin |

(56) References Cited

U.S. PATENT DOCUMENTS

| | | |
|---|---|---|
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,645,223 B2 | 11/2003 | Boyle et al. |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert |
| 6,719,763 B2 | 4/2004 | Chung et al. |
| 6,726,701 B2 | 4/2004 | Gilson et al. |
| 6,738,656 B1 | 5/2004 | Ferre et al. |
| 6,740,191 B2 | 5/2004 | Clarke et al. |
| 6,741,884 B1 | 5/2004 | Freeman et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,785,857 B1 | 8/2004 | Ishikawa |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,860,264 B2 | 3/2005 | Christopher |
| 6,860,849 B2 | 3/2005 | Matsushita et al. |
| 6,866,669 B2 | 3/2005 | Buzzard et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,953,431 B2 | 10/2005 | Barthel |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartagalia et al. |
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,037,321 B2 | 5/2006 | Sachdeva et al. |
| 7,043,961 B2 | 5/2006 | Pandey |
| 7,044,964 B2 | 5/2006 | Jang et al. |
| 7,048,711 B2 | 5/2006 | Rosenman et al. |
| 7,052,474 B2 | 5/2006 | Castell et al. |
| 7,056,284 B2 | 6/2006 | Marton et al. |
| 7,056,287 B2 | 6/2006 | Taylor et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |

(56) References Cited

U.S. PATENT DOCUMENTS

| | | |
|---|---|---|
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,309,334 B2 | 12/2007 | von Hoffmann |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,384,407 B2 | 6/2008 | Rodriguez et al. |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,551,758 B2 | 6/2009 | Florent et al. |
| 7,559,925 B2 | 7/2009 | Goldfarb et al. |
| 7,566,300 B2 | 7/2009 | Devierrre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,751,758 B2 | 7/2010 | Yahagi |
| 7,753,929 B2 | 7/2010 | Becker |
| 7,753,930 B2 | 7/2010 | Becker |
| 7,758,497 B2 | 7/2010 | Hern |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Rossner et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,475,360 B2 | 7/2013 | Brown |
| 8,521,259 B2 | 8/2013 | Mandrusov et al. |
| 8,529,439 B2 | 9/2013 | Ito et al. |
| 8,535,707 B2 | 9/2013 | Arensdorf et al. |
| 8,568,439 B2 | 10/2013 | Keith et al. |
| 8,585,728 B2 | 11/2013 | Keith et al. |
| 8,585,753 B2 | 11/2013 | Scanlon et al. |
| 8,864,787 B2 | 1/2014 | Muni et al. |
| 8,702,626 B1 | 4/2014 | Kim et al. |
| 8,715,169 B2 | 5/2014 | Chang et al. |
| 8,718,786 B2 | 5/2014 | Shalev |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,777,926 B2 | 7/2014 | Chang et al. |
| 8,802,131 B2 | 8/2014 | Arensdorf et al. |
| 8,828,041 B2 | 9/2014 | Chang et al. |
| 8,858,586 B2 | 10/2014 | Chang et al. |
| 8,858,974 B2 | 10/2014 | Eaton et al. |
| 8,894,614 B2 | 11/2014 | Muni et al. |
| 8,932,276 B1 | 1/2015 | Morriss et al. |
| 8,951,225 B2 | 2/2015 | Evard et al. |
| 8,961,398 B2 | 2/2015 | Makower et al. |
| 9,039,657 B2 | 5/2015 | Makower et al. |
| 9,055,965 B2 | 6/2015 | Chang et al. |
| 9,101,739 B2 | 8/2015 | Lesch, Jr. et al. |
| 9,167,961 B2 | 10/2015 | Makower et al. |
| 9,179,823 B2 | 11/2015 | Goldfarb et al. |
| 9,216,112 B2 | 12/2015 | Clifford et al. |
| 9,220,879 B2 | 12/2015 | Chang et al. |
| 9,241,834 B2 | 1/2016 | Chang et al. |
| 9,265,407 B2 | 2/2016 | Goldfarb et al. |

(56) References Cited

U.S. PATENT DOCUMENTS

| | | |
|---|---|---|
| 9,289,576 B2 | 3/2016 | Mann et al. |
| 9,308,361 B2 | 4/2016 | Muni et al. |
| 9,370,649 B2 | 6/2016 | Chang et al. |
| 9,399,121 B2 | 7/2016 | Goldfarb et al. |
| 9,603,506 B2 | 3/2017 | Goldfarb et al. |
| 9,610,428 B2 | 4/2017 | Muni et al. |
| 9,649,477 B2 | 5/2017 | Muni et al. |
| 2001/0004644 A1 | 6/2001 | Levin |
| 2001/0005785 A1 | 6/2001 | Sachse |
| 2001/0034530 A1 | 10/2001 | Malackowski et al. |
| 2002/0006961 A1 | 1/2002 | Katz et al. |
| 2002/0013548 A1 | 1/2002 | Hinchliffe |
| 2002/0055746 A1 | 5/2002 | Burke et al. |
| 2002/0068851 A1 | 6/2002 | Gravenstein et al. |
| 2002/0077593 A1 | 6/2002 | Perkins et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0073900 A1 | 4/2003 | Senarith et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0038319 A1 | 2/2005 | Goldwasser et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228224 A1 | 10/2005 | Okada et al. |
| 2005/0234507 A1 | 10/2005 | Geske et al. |
| 2005/0244472 A1 | 11/2005 | Hughes et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0167682 A1 | 7/2007 | Goldfarb et al. |
| 2007/0208252 A1 | 9/2007 | Makower |
| 2007/0269385 A1 | 11/2007 | Yun et al. |
| 2007/0293946 A1 | 12/2007 | Gonzales et al. |
| 2008/0033519 A1 | 2/2008 | Burwell et al. |
| 2008/0051804 A1 | 2/2008 | Collier et al. |
| 2008/0103521 A1 | 5/2008 | Makower et al. |
| 2008/0172033 A1 | 7/2008 | Keith et al. |
| 2008/0188803 A1 | 8/2008 | Jang |
| 2008/0188870 A1 | 8/2008 | Andre et al. |
| 2008/0228085 A1 | 9/2008 | Jenkins et al. |
| 2008/0275483 A1 | 11/2008 | Makower et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2010/0087811 A1 | 4/2010 | Herrin et al. |
| 2010/0198191 A1 | 8/2010 | Clifford et al. |
| 2010/0198247 A1 | 8/2010 | Chang et al. |
| 2011/0060214 A1 | 3/2011 | Makower et al. |
| 2014/0200444 A1 | 7/2014 | Kim et al. |
| 2014/0296898 A1 | 10/2014 | Chang et al. |
| 2014/0330074 A1 | 11/2014 | Morriss et al. |
| 2014/0336693 A1 | 11/2014 | Goldfarb et al. |
| 2014/0350465 A1 | 11/2014 | Muni et al. |
| 2014/0364725 A1 | 12/2014 | Makower |
| 2015/0165175 A1 | 6/2015 | Evard et al. |
| 2015/0165176 A1 | 6/2015 | Makower et al. |
| 2015/0182735 A1 | 7/2015 | Chang et al. |
| 2015/0250992 A1 | 9/2015 | Morriss et al. |
| 2016/0192830 A1 | 7/2016 | Goldfarb et al. |
| 2016/0270863 A1 | 9/2016 | Makower |
| 2017/0007281 A1 | 1/2017 | Goldfarb et al. |
| 2017/0071625 A1 | 3/2017 | Chang et al. |

FOREIGN PATENT DOCUMENTS

| | | |
|---|---|---|
| CN | 2151720 | 1/1994 |
| CN | 2352818 | 12/1999 |
| CN | 201005758 Y | 1/2008 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1112103 | 7/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | S61-16750 A | 1/1986 |
| JP | 10-24098 | 1/1989 |
| JP | 10-034376 | 2/1989 |
| JP | H01-305965 A | 12/1989 |
| JP | 3-503011 | 7/1991 |
| JP | 3-504935 | 10/1991 |
| JP | 4-221313 | 8/1992 |
| JP | 4-224766 | 8/1992 |
| JP | 5-503650 | 6/1993 |
| JP | 5-211985 | 8/1993 |
| JP | H05-506805 A | 10/1993 |

(56) References Cited

FOREIGN PATENT DOCUMENTS

| | | |
|---|---|---|
| JP | H6-017751 | 3/1994 |
| JP | 6-277296 | 10/1994 |
| JP | 7-327916 | 12/1995 |
| JP | 8-317989 | 12/1996 |
| JP | H10-501159 A | 2/1998 |
| JP | H10-94543 | 4/1998 |
| JP | 11-507251 | 6/1999 |
| JP | 2000-501634 | 2/2000 |
| JP | 2000-126303 | 5/2000 |
| JP | 2001-025508 A | 1/2001 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/82800 | 11/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int. J. Pediatric Otorhinolaryngol (1991) vol. 21 pp. 97-101.
Gerus, I.I. et al. 'ß-Ethoxyvinyl Polyfluroroalkyl Ketones—Versatile Synthones in Fluoroorganic Chemistry' Journal of Fluorine Chemistry. vol. 69 (1994) pp. 195-198. Elesvier Sciences S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Pharm. Biophar. vol. 42 (1996) pp. 1-11.
Gorlov, D.V. et al 'Acylation of 2-Methoxypropene with Anhydrides and Halides of Perflurocarboxylic Acids in the Presenceot Teriary Amines' Russian Chemical Bulletin. vol. 48 No. 9 (Sep. 1999) pp. 1791-1792. Kluwer Academic/Plenum Publishers.
Gottman, et al., Balloon Dilatation of Recurrent Ostial Occlusion of the Front Sinus' OASIS—Online Abstract Submission and Invitation System, 1996-2006, Coe Truman Technologies, Inc.
Gottmann, D. 'Treatment of Stenoses of Upper Air Routes by Balloon Dilation' Proceeding of the 83rd Annual Convention of Association of West German ENT Physicians (1999).
Gottmann, et al. 'Balloon Dilatation of Recurrent Ostial Occlusion of the Frontal Sinus'CIRSE Abstract (Mar. 2001) B-04353.
Gottmann, et al. 'Balloon Dilatation in the Nasal Cavity and Paranasal Sinuses' CIRSE. (Sep. 25, 2004) pp. 1-27.
Gottmann, et al. 'Successful Treatment of Recurrent Post-Operative Frontal Sinus Stenoses by Balloon Dilatation' CIRSE. (Oct. 5, 2002).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle ethers and N Vinyl Amides Chemistry Letters' (1976) pp. 499-502. Chemical Society of Japan.
Hopf, J.U.G. et al. 'Minature Endoscopes in Otorrhinolaryngologic Applications' Min Invas Ther & Allied Technol. (1998) vol. 7, No. 3 pp. 209-218.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54.
Hosemann, M.E. et 31. 'Normal Wound Healing of the Paranasal Sinuses-Clinical and Experimental Investigations' Eur Arch Otorhinolarygol. vol. 248, (1991) pp. 390-394.
Hosemann, W. et al. A Dissection Course on Endoscopic Endonasal Sinus Surgery (2005) Endo-Press, Tuttlingen pp. 4-37.

(56) References Cited

OTHER PUBLICATIONS

Hosemann, W. et al. 'Behandlung nach Nasennebenhohleneingriffen, part 2: Theapeutische Maßnahem' HNO akutell 7 (1999) pp. 291-302.

Hosemann, W. et al. 'Endonasal Frontal Sinusotomy in Surgical Management of Chronic Sinusitis: A Critical Evaluation' American Journal of Rhinology. vol. 11, No. (1997) pp. 1-9.

Hosemann, W. G. et al. 'Minimally Invasive Endonasal Sinus Surgery' Thieme, Stuttgart, New York (2000).

Hospital Corpsman Sickcall Screener's Handbook, Naval Hospital Great Lakes (Apr. 1999) www.brooksidepress.org/Products/Operationa.Medicine/DATA. 2001 pp. 1-6.

Hybels, R.L. 'Transillumination During Osteoplastic Frontal Sinusotomy' The Laryngoscope. vol. 91 (Sep. 1981) pp. 1560.

Ijaduola, T.G.A. 'Use of a Foley Catheter for Short-Term Drainage in Frontal Sinus Surgery' TherJournal of Laryngology and Otology. (1989) vol. 103. pp. 375.378.

Ingals, E.F. 'New Operation and Instruments for Draining th eFrontal Sinus' Ann. Otol. Rhinol. Layyngol. vol. 14 (1905) pp. 644-649.

Iro, H. et al., 'A New Device for Frontal Sinus Endoscopy. First Clinical Report' Otolaryngol. Head Neck Surg. (2001) vol. 125 No. 6 pp. 613-616.

Jacobs, J.B. '100 Years of Frontal Sinus Surgery' Laryngoscope. vol. 107 (1997) pp. 1-36.

K-Splint Internal Nasal Splints; Jan. 25, 2007; www.invotec.net/rhinology/ksplint.html.

Kaiser, H. et al 'Cortizontherapic, Corticoide in Klinik und Praxis' Thieme, Stuggart (1992) pp. 390-401.

Kennedy, D.W., M.D. et al. 'Diseases of the Sinuses: Diagnosis and Management' (Copyright 2001) by B.C. Decker Inc.

Khomutov, S.M. et al. 'Dissolution of a Mixture of Steroids in Cyclodextrin Solutions: A Model Description' Pharmaceutical Chemistry Journal. vol. 35, No. 11 (Nov. 2001) pp. 627-629.

Kingdom, T.T. et al. 'Image-Guided Surgery of the Sinuses: Current Technology and Applications' Otolaryngol. Clin. North Am. vol. 37, No. 2 (Apr. 2004) pp. 381-400.

Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology, vol. 39, No. 1 (2001) pp. 17-22.

Argon Medical. Maxxim Medical. Ad for Sniper EliteTM Hydrophilic Ni—Ti Alloy Guidewire (2001).

Aust, R., et al. 'The Functional Size of the Human Maxillary Ostium in Vivo' Acta. Otolaryn. (1974) vol. 78 pp. 432-435.

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chriobase.org/06DD/ncr.html.

Bartal, N. 'An Improved stent for Use in the Surgical Management of Congential Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.

Bellis, M., History of the Catheter-Balloon Catheter-Thomas Fogarty, 2006, www.inventors.about.com/library/inventors/blcatheter.htm?p=1.

Benninger et al.; Adult Chronic Rhinosinusitis: Defintions, Diagnosis, Epidemiology, and Pathophysilogy' Arch Otolaryngol Head and Neck Surg. vol. 129 (Sep. 2003) pp. A1-S32.

Bent et al. 'The Frontal cell as a Cause of Frontal Sinus Obstruction' American Journal of Rhinology, vol. 8, No. 4 (1994) pp. 185-191.

Binner et al. 'Fibre-Optic Transillumination of the Sinuses: A Comparison of the Value of Radiography and Transillumination in Antral Disease' Clinical Otolaryngology, vol. 3 (1978) pp. 1-11.

Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.

Casiano et al. 'Endoscopic Lothrop Procedure: the University of Miami Experience' American Journal of Rhinology, vol. 12, No. 5 (1998) pp. 335-339.

Casserly, I.P. et al., Chapter 7, 'Guides and Wires in Percutaneous Coronary Intervention' Strategic Approaches in Coronary Intervention (2006) Lippincott Williams & WIlkins pp. 91-99.

Chien, Y.W. et al. 'Nasal Systemic Drug Delivery' Drugs and Pharmaceutical Sciences, vol. 39, 1989, pp. 60-63.

Cohen et al. 'Endoscopic Sinus Surgery: Where we are and where we're going' Current Opinion in Otolaryngology & Head and Neck Surgery, vol. 13 (2005) pp. 32-38.

Colla, A. et al., 'Trihaloacety lated Enol Ethers-General Synthetic Procedure and Heterocyclic Ring Closure Reactions with Hydroxylamine' Synthesis, (Jun. 1991) pp. 483-486.

Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.

Cussler, E.L. 'Diffusion: Mass transfer in Fluid Systems' Cambridge University Press(1996).

Davis, G.E. et al. 'A Complication from Neurocranial Restructuring' Arch Otolaryngol Head Neck Surg. vol. 129 (Apr. 2003) pp. 472-474.

Deutschmann, R. et al. 'A Contribution to the Topical Treatment of [Maxillary] Sinusitis Preliminary Communication' Stomat DDR 26, (1976) pp. 585-592.

Domb, A. et al. 'Handbook of Biodegradable Polymers' Harwood Academic Publishers (1997).

Doyle Nasal Splints, Jan. 25, 2007; www.doylemedical.com/nasalsplints.htm.

Draf, W. 'Endonasal Micro-Endoscopic Frontal Sinus Surgery: the Fulda Concept' Op Tech Otolaryngol Head Neck Surg. vol. 2 (1991) pp. 234-240.

Edmond, C. et al. 'ENT Surgical Stimulator' Nov. 1989.

ENT Checklist; Physical Examination Performance Checklist [date of publication unknown].

Eremychev, V.A. 'Needles for Puncture and Drainage of the Maxillary Sinus' Meditsinskaya Tekhnika, No. 5 (1974) pp. 54.55.

'Experimental investigations on wound healing of the paranasal sinuses. II. Spontaneous wound closure and pharmacological effects in a standardized animal model.' HNO 39 (1991) pp. 48-54.

Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.

Ford, C.N. 'A Multipurpose Laryngeal Injector Device' Otolaryngol. Head Neck Surg. (1990) vol. 103, No. 1 pp. 135-137.

Friedman, et al 'Middle Turbinate Medialization and Preservation in Endoscopic Surgery' Otolaryngology—Head and Neck Surgery. (2000) vol. 123, No. 1, part 1, pp. 76-80.

Friedman, et al. 'Intraoperative and Postoperative Assessment of Frontal Sinus Patency by Transillumination' Laryngoscope. vol. 110 (Apr. 2000) pp. 683-684.

Shah, N.J. 'Functional Endoscopic Sinus Surgery' (1991); found at bhj.org/journal/1999_4104-oct99/sp_659.htm.

Single-Pole and Multi-Pole Lightguides for UV Spot Light Curing Systems, www.dymax.com/products/curing_equipment/lightguids/light, 2004, pp. 1-2.

Sinusitis, Maxillary, Acute Surgical Treatment, Http://www.emedicine.com/ent/topic340.htm. Aug. 29, 2006. pp. 1-11.

Sobol, et al. 'Sinusitis, Maxillary, Acute Surgical Treatment.' eMedicine. Retrieved from the Internet: <<http://emedicine.medscape.com/article/862030-print>>(Nov. 16, 2010) pp. 1-11.

St. Croix et al. 'Genes Expressed in Human Tumor Endothelium'Science, vol. 289 (May 15, 2000) pp. 1197-1202.

Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.

Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.

(56) References Cited

OTHER PUBLICATIONS

Strohm, et al 'Le Traitenment Des Stenoses Voies Aeriennes Superieures Par Dilation Ay Balloon' Sep. 25, 1999.
Strohm, et al. Die Behandlung von Stenosen der oberen Luftwege mittels rontgenologisch gesteuerter Ballondilation (Sep. 25, 1999) pp. 1-4.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.nejp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Endoscopy (UK) Ltd.' 2005, p. 4.
Weber, R. et al. 'Endonasale Stirnhohlenchirugie mit Langeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action dated Feb. 12, 2014 for Application No. AU 2012202103.
Australian Office Action dated Aug. 1, 2014 for Application No. AU 2012244072.
Australian Office Action dated Sep. 17, 2014 for Application No. AU 2012202103.
Australian Office Action dated Sep. 30, 2014 for Application No. AU 2009293312.
Australian Office Action dated Oct. 1, 2014 for Application No. AU 2009333010.
Australian Office Action dated Jul. 8, 2015 for Application No. AU 2012244072.
Canadian Office Action dated Jul. 10, 2015 for Application No. CA 2,617,054.
Canadian Office Action dated Dec. 16, 2015 for Application No. CA 2,751,665.
Chinese Search Report dated Jan. 11, 2013 for Application No. CN 200980152995.0.
Chinese Office Action, First Office Action dated Jan. 29, 2013 for CN 200980152995.1.
Chinese Office Action, Decision of Rejection, dated 2014 for Application No. CN 200980152995.1.
Chinese Office Action, Third Office Action, dated Feb. 27, 2014 for Application No. CN 200980152995.1.
Chinese Search Report dated Oct. 29, 2012 for Application No. CN 200980137396.1.
Chinese Office Action, First Office Action dated Nov. 5, 2012 for CN 200980137396.1.
Kozlov et al. 'Diagnosis and Treatment of Sinusitis by Yamik Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser. Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Metson, R., et al., 'Endoscopic Treatment of Sphenoid Sinusitis' Otolaryngol. Head Neck Surg. (1996) vol. 114, No. 6 pp. 736-744.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.

(56) References Cited

OTHER PUBLICATIONS

Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.
Sama, A., et al., 'Current Opinions on the Surgical Management of Frontal Sinus Disease' Ent News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Supplemental European Search Report dated Feb. 13, 2014 for Application No. EP 08746464.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
International Search Report and Written Opinion dated Apr. 10, 2006 for Application No. PCT/US2005/25371.
International Preliminary Report on Patentability dated Aug. 7, 2006 for Application No. PCT/US2005/25371.
International Search Report and Written Opinion dated Jul. 21, 2008 for Application No. PCT/US2005/033090.
International Search Report and Written Opinion dated Sep. 12, 2008 for Application No. PCT/US2007/16214.
International Search Report and Written Opinion dated Sep. 17, 2008 for Application No. PCT/US2008/059786.
International Preliminary Report on Patentability and Written Opinion dated Oct. 13, 2009 for Application No. PCT/US2008/059786.
International Search Report and Written Opinion dated Sep. 17, 2008 for Application No. PCT/US2008/061343.
International Preliminary Report on Patentability and Written Opinion dated Oct. 27, 2009 for Application No. PCT/US2008/061343.
International Search Report and Written Opinion dated Oct. 1, 2008 for Application No. PCT/US2007/011449.
International Search Report dated May 8, 2007 for Application No. PCT/US2006/16026.
International Search Report dated Aug. 17, 2007 for Application No. PCT/US2005/013617.
International Preliminary Report on Patentability dated Feb. 15, 2008 for Application No. PCT/2005/13617.
International Search Report dated Aug. 29, 2007 for Application No. PCT/US2006/002004.
International Preliminary Report on Patentability and Written Opinion dated Sep. 25, 2007 for Application No. PCT/US2006/002004.
International Search Report dated Sep. 25, 2007 for Application No. PCT/US2006/037167.
International Search Report dated Oct. 19, 2007 for Application No. PCT/US2007/003394.
International Search Report dated May 29, 2008 for Application No. PCT/US2007/021170.
International Preliminary Report on Patentability and Written Opinion dated Nov. 18, 2008 for Application No. PCT/US2007/11449.
International Search Report and Written Opinion dated Oct. 6, 2010 for Application No. PCT/US2010/040548.
International Search Report dated Jun. 3, 2002 for Application No. PCT/EP2002/01228.
International Preliminary Report on Patentability and Written Opinion dated Apr. 7, 2009 for Application No. PCT/2007/021170.
International Search Report dated May 29, 2008 for Application No. PCT/US2007/021922.
International Search Report dated Jul. 1, 2008 for Application No. PCT/US2006/022745.
International Search Report dated Jul. 3, 2008 for Application No. PCT/US2006/029695.
International Search Report dated Jul. 7, 2008 for Application No. PCT/US2007/016213.
International Search Report dated Jul. 8, 2008 for Application No. PCT/US2007/011474.
International Search Report dated Jul. 17, 2008 for Application No. PCT/US2006/036960.
International Preliminary Report on Patentability and Written Opinion dated May 5, 2009 for Application No. PCT/US2006/036960.
International Search Report dated Aug. 25, 2008 for Application No. PCT/US2008/000911.
International Search Report dated Sep. 10, 2008 for Application No. PCT/US2007/016212.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Preliminary Report on Patentability dated Jun. 29, 2011 for Application No. PCT/US2009/069143.
International Search Report dated Jul. 8, 2010 for Application No. PCT/US2010/027837.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Written Opinion dated Aug. 9, 2011 for Application No. PCT/US2011/038751.
International Search Report dated May 18, 2012 for Application No. PCT/US2011/052321.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.

(56) References Cited

OTHER PUBLICATIONS

Japanese Office Action, Examiner's Decision of Refusal dated Oct. 18, 2011 for Application No. JP 2007-509632.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Japanese Office Action, Notification of Reasons for Refusal dated Sep. 18, 2013 for Application No. JP 2011-527942.
Chinese Office Action and Search Report dated Jan. 21, 2015 for Application No. CN 201310672731.6.
English Machine Translation of Japanese Patent Publication No. JP5-503650, Jun. 17, 1993.
European Communication dated Sep. 4, 2008 for Application No. EP 05773189.
European Communication dated Jun. 19, 2009 for Application No. EP 05773189.
European Communication dated Sep. 27, 2011 for Application No. EP06800540.4.
European Communication dated Apr. 19, 2012 for Application No. EP 08746715.5.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Communication dated Sep. 3, 2013 for Application No. EP 12182998.0.
European Communication dated Feb. 26, 2014 for Application No. EP 06800540.4.
European Communication dated Aug. 11, 2014 for Application No. EP 12182998.0.
European Communication dated Aug. 26, 2014 for Application No. EP 12183000.4.
European Communication dated Nov. 26, 2014 for Application No. EP 07836108.6.
European Communication dated Feb. 17, 2016 for Application No. EP 12162712.9.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 for Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. Ep 12183002.
European Search Report dated Aug. 13, 2013 for Application No. EP 13172140.
European Search Report dated Sep. 9, 2013 for Application No. EP 13179223.
European Search Report dated May 19, 2015 for Application No. EP 08746464.0.
European Search Report dated Jun. 23, 2015 for Application No. EP 12162712.9.
European Search Report dated Jun. 23, 2015 for Application No. EP 12162709.5.
Extended European Search Report dated Jan. 17, 2014 for Application No. EP 108426321.1.
Extended European Search Report dated Sep. 15, 2015 for Application No. EP 15163549.7.
Partial European Search Report dated Mar. 25, 2008 for Application No. EP 07252018.
Partial European Search Report dated Sep. 20, 2007 for Application No. EP 07252018.
Supplemental European Search Report dated Jan. 14, 2014 for Application No. EP 13184009.
Supplemental European Search Report dated Jan. 17, 2014 for Application No. EP 1084263.
Supplemental European Search Report dated Dec. 9, 2014 for Application No. EP 07839152.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.

(56) References Cited

OTHER PUBLICATIONS

USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.
U.S. Appl. No. 11/804,308, filed May 16, 2007.
Japanese Office Action, Notification of Reasons for Refusal dated Sep. 18, 2013 for Application No. JP 2011-542562.
Japanese Office Action, Notification of Reasons for Refusal dated Sep. 7, 2014 for Application No. JP 2012-266049.
Japanese Office Action, Reasons for Refusal, dated Sep. 2, 2014 for Application No. JP 2012-544859.
Japanese Office Action, Reasons for Refusal, dated Jun. 9, 2015 for Application No. JP 2014-147174.
Partial International Search Report dated Feb. 7, 2012 for Application No. PCT/US2011/052321.
Russian Office Action dated Mar. 19, 2013 for Application No. RU 2011130530.
Russian Office Action dated Sep. 28, 2012 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
Supplemental European Search Report dated Mar. 24, 2010 for Application No. EP 07836108.6, 6 pgs.
Supplemental European Search Report and Written Opinion dated Sep. 8, 2011 for Application No. EP 06800540.4, 11 pgs.
Supplemental European Search Report dated Feb. 27, 2014 for Application No. EP 08746464.0, 11 pgs.
European Communication dated Sep. 26, 2016 for Application No. EP 12162712.9, 4 pgs.
Japanese Office Action, Notification of Reasons for Refusal dated Mar. 29, 2016 for Application No. JP 2012-266049, 6 pgs.
U.S. Appl. No. 15/417,655, filed Jan. 27, 2017.
U.S. Appl. No. 15/417,712, filed Jan. 27, 2017.
U.S. Appl. No. 15/443,319, filed Feb. 27, 2017.

DEVICES, SYSTEMS AND METHODS USEABLE FOR TREATING FRONTAL SINUSITIS

RELATED APPLICATIONS

This application is a continuation of U.S. patent application Ser. No. 14/515,687 entitled "Devices, Systems and Methods Useable for Treating Frontal Sinusitis" filed Oct. 16, 2014, issued on Apr. 4, 2017 as U.S. Pat. No. 9,610,428, which is a continuation of 11/355,512 entitled "Devices, Systems, and Methods Useable for Treating Frontal Sinusitis" filed Feb. 16, 2006, issued Nov. 5, 2014 as U.S. Pat. No. 8,894,614, which is a continuation-in-part of U.S. patent application Ser. No. 11/150,847 entitled "Devices, Systems and Methods Useable for Treating Sinusitis" filed on Jun. 10, 2005, issued Sep. 28, 2010 as U.S Pat. No. 7,803,150, which is a continuation in part of U.S. patent application Ser. No. 10/944,270 entitled "Apparatus and Methods for Dilating and Modifying Ostia of Paranasal Sinuses and Other Intranasal or Paranasal Structures" filed on Sep. 17, 2004, published as U.S. Pub. No. 2006/0004323 on Jan. 5, 2006, now abandoned, which is a continuation-in-part of U.S. patent application Ser. No. 10/829,917 entitled "Devices, Systems and Methods for Diagnosing and Treating Sinusitis and Other Disorders of the Ears, Nose and/or Throat" filed on Apr. 21, 2004, issued Feb. 2, 2010 as U.S. Pat. No. 7,654,997, the entire disclosures of such earlier filed applications being expressly incorporated herein by reference.

FIELD OF THE INVENTION

The present invention relates generally to medical devices and methods and more particularly to minimally invasive, devices, systems and methods for treating sinusitis and other ear, nose & throat disorders.

BACKGROUND

In human beings, the frontal paranasal sinuses reside on either side of the forehead adjacent to and above the orbits. The right and left frontal sinuses are divided by an intersinus septum. Each frontal sinus has a natural opening (i.e., an ostium) formed in the posteromedial aspect of the sinus floor. In most patients, a narrow anatomical pre-chamber known as the frontal recess extends between the frontal sinus ostium and the nasal cavity. The frontal recess is a bony structure covered by mucosal tissue. The anterior border of the frontal recess is formed by the posterior wall of the agger nasi cell and the medial aspect of the frontal recess relates to the lateral lamella of the cribriform and the cribriform plate. Mucous normally drains out of the frontal sinus ostium, through the frontal recess, and into the nasal cavity. The ostium and frontal recess are sometimes referred to in combination as the frontal outflow tract (FOT). In many individuals, the FOT is a relatively long passage.

In patients suffering from acute frontal sinusitis, the FOT may become inflamed and occluded, thereby impeding natural drainage from the frontal sinus cavity and allowing infectious organisms to thrive within the frontal sinus cavity and associated ethmoid air cells. Acute frontal sinusitis is sometimes associated with intracranial and/or ocular complications. Ocular complications that are known to result from frontal sinusitis include thrombosis, thrombophlebitis, cellulites and orbital abscesses. One type of orbital abscess, known as a Pott puffy tumor, is associated with considerable soft tissue swelling over the frontal bone. Intracranial complications associated with frontal sinusitis include meningitis, brain abscess, epidural empyema, subdural empyema, and cerebral empyema.

In current practice, surgical procedures are performed for the treatment of acute frontal sinusitis only after the condition has failed to respond to conservative therapy (e.g., administration of antibiotics and mucolytic agents along with topical steroids and topical or systemic decongestants) or when other complications are present or when the infection has recurred more than 3-4 times in a year. The surgical procedures used to treat acute frontal sinusitis include functional endoscopic sinus surgery (FESS) procedures as well as open surgical procedures.

In FESS procedures, a nasal endoscope and other instruments (e.g., seekers, probes, rongeurs, a drills, and bony curettes) are inserted transnasally and used to improve patency of the FOT or otherwise improve drainage from the diseased frontal sinus. This process often involves the performace of an uncinectomy, anterior ethmoidectomy, agger nasi removal, and/or resection of the anterosuperior attachment of the middle turbinate. In some cases, the superior aspect of the nasal septum may be removed in a bilateral frontal sinus drill-out procedure. In many frontal sinus FESS procedures, disease of the anterior ethmoids is also be addressed during the surgery. In some cases, a stent is placed within the surgically altered FOT to maintain its patency in the weeks following the surgery. In cases where a stent is implanted, the patient is typically advised to irrigate the stent several times a day for up to 5-7 weeks after the surgery.

Postoperatively, it is typically necessary for FESS patients to visit the surgeon periodically for postoperative care, such as debridement, removal of clots, removal of granulation tissue, removal of crust, removal of polyps, etc.

FESS treatment of frontal sinusitis does have some disadvantages. For example, the FESS procedures are technically complex, accessing disease in the supraorbital frontal sinus cell is difficult, postoperative care can be laborious, confirming the patency of the surgically altered FOT may be difficult during the initial postoperative period.

Moreover, given the risks associated with the FESS procedure, some patients with relatively mild frontal sinusitis are not considered to be candidates for the procedure even though the available medical therapies may provide them with less than complete relief.

In the trephination procedure, a small supraorbital incision is made below the medial eyebrow and the underlying periosteum is elevated. A bore hole is then made through the skull bone and into the sinus cavity. The interior or the sinus may then be cleaned and small tubes may be inserted and used for future irrigation or drainage. In some cases, trephination may be performed concurrently with endoscopic frontal sinus surgery. In some patients, the intersinus septum may be removed and a single opening may be created through which both frontal sinuses may drain into the nasal cavity. The main contraindication to the trephination procedure is the presence of an aplastic frontal sinus.

Other open surgeries, known generally as frontoethmoidectomies, have also been used to treat frontal sinusitis and associated ethmoid disease. These procedures have been performed by various approaches, including those known as the Lynch approach, the Killian method, the Reidel method and the Lathrop or Chaput-Meyer approach.

Another group of open procedures used to treat frontal sinusitis are known generally as osteoplastic flap procedures. These osteoplastic flap procedures are typically employed only in severe cases where frontal sinusitis is refractory or accompanied by intracranial complications.

Osteoplastic flap procedures have been performed by various approaches, including a coronal approach, a midline forehead approach and a brow incision approach. After an initial incision is made by one of these three approaches, a template may be used to outline the frontal sinus. An incision is then made through the periosteum at a location slightly above the outline of the sinus. The periostium is elevated and a saw is used to cut into the frontal sinus. Small cuts may also be made above the glabella to loosen the frontonasal suture. In this manner, an osteomeatal flap is created, exposing the interior of the frontal sinus. The surgeon may then remove the diseased sinus mucosa and may also alter the structure of the sinus and/or FOT, such as by removal of the intersinus septum. The remaining frontal sinus cavity is then packed with autogenous fat or other materials (Gelfoam, Teflon, fat, paraffin, silastic sponge, and cartilage), the osteomeatal flap is replaced and the periostium and skin layers are then closed with sutures. Some modified versions of the osteoplastic flap procedure also include the use of a pericranial flaps and/or cancellous bone grafts.

In general, open surgical procedures do provide excellent visualization of the interior of the sinus, thereby enabling the surgeon to see and correct a variety of problems. However, these open procedures can be extremely invasive. They also result in at least some visible scarring and typically involve substantial obliteration of existing anatomy to create an open frontonasal communication.

The prior art has included some disclosure of the use of balloon catheters to dilate anatomical passages and improve drainage from paranasal sinuses. For example, U.S. Pat. No. 2,525,183 (Robison) discloses an inflatable pressure device which can be inserted following sinus surgery and inflated within the sinus. Also, United States Patent Publication No. 2004/0064150 A1 (Becker), now U.S. Pat. No. 8,317,816, issued on Nov. 27, 2012, discloses balloon catheters wherein a balloon is mounted on a stiff hypotube that may purportedly be pushed into a sinus. The stiff hypotube has a fixed pre-set curve or angle. Additionally, an abstract entitled Balloon Dilatation of Recurrent Ostial Occlusion of the Frontal Sinus, by D. Gottmann, M. Strohm, E.-P. Strecker and D. E. Karlsruhe describes balloon dilatation of recurrent ostial occlusion of the frontal sinus in seven patients suffering from recurring chronic frontal sinusitis who had undergone between two and four prior surgeries for the condition. Using endonasal access the ostium of the frontal sinus was crossed with an angiographic catheter and a hydrophilic guidewire under fluoroscopic control. Then, the stenosed ostium was dilated with a high pressure percutaneous transluminal angioplasty balloon having a deflated diameter of 5 mm and an inflated diameter of 8 mm. This procedure was performed 2 to 8 times in each patient, at intervals of 2 to 12 weeks. The abstract reports that all of these procedures were technically successful and there were no complications. Although the prior art does disclose some uses of balloons to dilate the ostia of paranasal sinuses, the prior art has not disclosed specifically sized or configured balloons or other dilators that may be used to dilate the entire length of a FOT (i.e., the frontal sinus ostium as well as an adjacent frontal recess) in a single step or without the need for repositioning and multiple inflations of the balloon.

Because the surgical treatments for frontal sinusitis are invasive and associated with various risks and complications, there remains a need for the development of new devices and techniques for treatment of frontal sinusitis with less trauma and less risk of complications. Also, since surgical treatments for frontal sinusitis are typically reserved for only severe or refractory cases, there remains a need for the development of new interventions that go beyond the previously available conservative treatments (e.g., medical therapy with antibiotics, steroids, mucolytics, saline lavage, etc.) but do not involve the tissue trauma.

SUMMARY OF THE INVENTION

The present invention provides improved dilator systems and methods wherein a dilator of suitable length is used to simultaneously dilate the frontal sinus ostia and frontal recesses, and optionally to dilate the ostia of other sinuses as well.

In accordance with an embodiment of the invention, there is provided a method for improving outflow through the frontal sinus ostium and adjacent frontal recess in a human or animal subject. This method generally comprises the steps of (A) providing a dilator that has a collapsed configuration and an expanded configuration, said dilator being of a length that is approximately as long as or longer than the length of the frontal sinus ostium and frontal recess combined; (B) positioning the dilator such that it occupies the frontal sinus ostium and at least substantially all of the frontal recess while in its collapsed configuration; and (C) causing the dilator to expand to its expanded configuration, thereby dilating the frontal sinus ostium and at least substantially all of the frontal recess. In some embodiments, the dilator may be mounted on a catheter and the catheter may be inserted transnasally and advanced to a location where the dilator is positioned with the frontal sinus ostium and substantially all of the adjacent frontal recess. The dilator may comprise a balloon or any other expandable structure (e.g., an expandable systems of wires, mesh, etc.). In embodiments where the dilator is a balloon, the balloon may be elongated and non-compliant or semi-compliant and, optionally, may be at least partially coated with a protective coating. Examples of materials of which the balloon may be formed include polyethylene terephthalate (PET), Nylon and those materials referred to in U.S. Pat. No. 5,264,260 (Saab) which is expressly incorporated herein by reference. Examples of protective coatings that may be used include but are not necessarily limited to those described in U.S. Pat. Nos. 5,599,576 (Opolski) and/or 5,766,158 (Opolski), both of which are expressly incorporated herein by reference. In some embodiments, the protective coating may comprise a matrix polymer and a reinforcing agent. In some embodiments, a primer layer may optionally be disposed between the balloon surface and the protective coating. The matrix polymer of the protective coating may, for example, comprise a urethane, acrylic or epoxy. The reinforcing agent may, for example, be lamellar, platelet, or fiber-like in structure and may have a higher surface hardness than the surface hardness of the material of which the balloon is formed. Such reinforcing agent may, for example, comprise a micaceous pigment, glass fiber, lamellar platelet, flake pigment, tungsten powder and/or fibers. In some embodiments, the protective coating may have a thickness in the range of about 0.1 mil to about 3 mil and in some embodiments such coating thickness may be in the range of about 0.5 mil to about 2 mil. In some embodiments, the protective coating may further include a crosslinking agent (e.g., aziridine, carbodiimide, urea formaldehyde, melamine formaldehyde condensate, epoxy, isocyanate, titanate, zircoaluminate, zinc crosslinker, silane, etc.). In some embodiments, the protective coating may further include an additive selected from the group consisting of radio pacifiers, antislip additives, anti-mar additives, and antimicrobial agents, and therapeutic agents or other therapeutic or diagnostic substances.

Further in accordance with the invention, there is provided a system that is useable to perform the above summarized method. Such system generally comprises a dilation catheter having a dilator as summarized hereabove and a guide (e.g., a tubular guide through which the dilation catheter is advanced or an elongate guide member such as a guidewire over which the dilation guide catheter is advanced). The guide is useable to guide the positioning of the dilator. In at least some embodiments, the guide may be of substantially fixed shape (e.g., manufactured to a predetermined shape or at least partially malleable so that the surgeon may bend it to a desired substantially fixed shape prior to insertion). In at least some embodiments where the guide has a substantially fixed shape, such shape will include a curve near the distal end of the guide to facilitate positioning of the distal end of the guide within or adjacent to the frontal recess. The guide is insertable through one of the subject's nostrils and advanceable to a position where the distal end of the guide is adjacent to or within the frontal recess. Thereafter, the dilation catheter is advanceable over or through the guide to a position where the dilator is positioned within the frontal sinus ostium and frontal recess (or other ostium or structure to be dilated). Thereafter, the dilator may be expanded to cause dilation of the frontal sinus ostium and substantially all of the adjacent frontal recess (or whatever other ostium or anatomical structure is to be dilated. In at least some embodiments, the dilation catheter may have a length of or less than 50 cm. In at least some embodiments, the dilation catheter may have a length of or less than 42 cm. In at least some embodiments, the dilation catheter may have a length of or less than 25 cm. Also, in at least some embodiments, the dilator may be less than 1 mm wide at its widest point while in its collapsed configuration and more than 3 mm wide at its widest point when in its expanded configuration. Also, the dilator itself may have a have a length of more than 10 mm (e.g., a 24 mm dilator may be used to dilate the frontal sinus ostium and substantially all of the adjacent frontal recess in most adult or fully grown humans. The dilator may comprise a balloon or any other expandable structure (e.g., an expandable systems of wires, mesh, etc.). In embodiments where the dialtor comprises a balloon the balloon may be constructed and/or coated as described in the preceding paragraph hereabove and in the U.S. Patents incorporated by reference therein.

Further aspects, details and embodiments of the present invention will be understood by those of skill in the art upon reading the following detailed description of the invention and the accompanying drawings.

BRIEF DESCRIPTION OF THE DRAWINGS

FIG. 3A shows a guidewire, FIG. 3B shows a dilation catheter and FIG. 3C shows a tubular guide.

DETAILED DESCRIPTION

Figure 1:
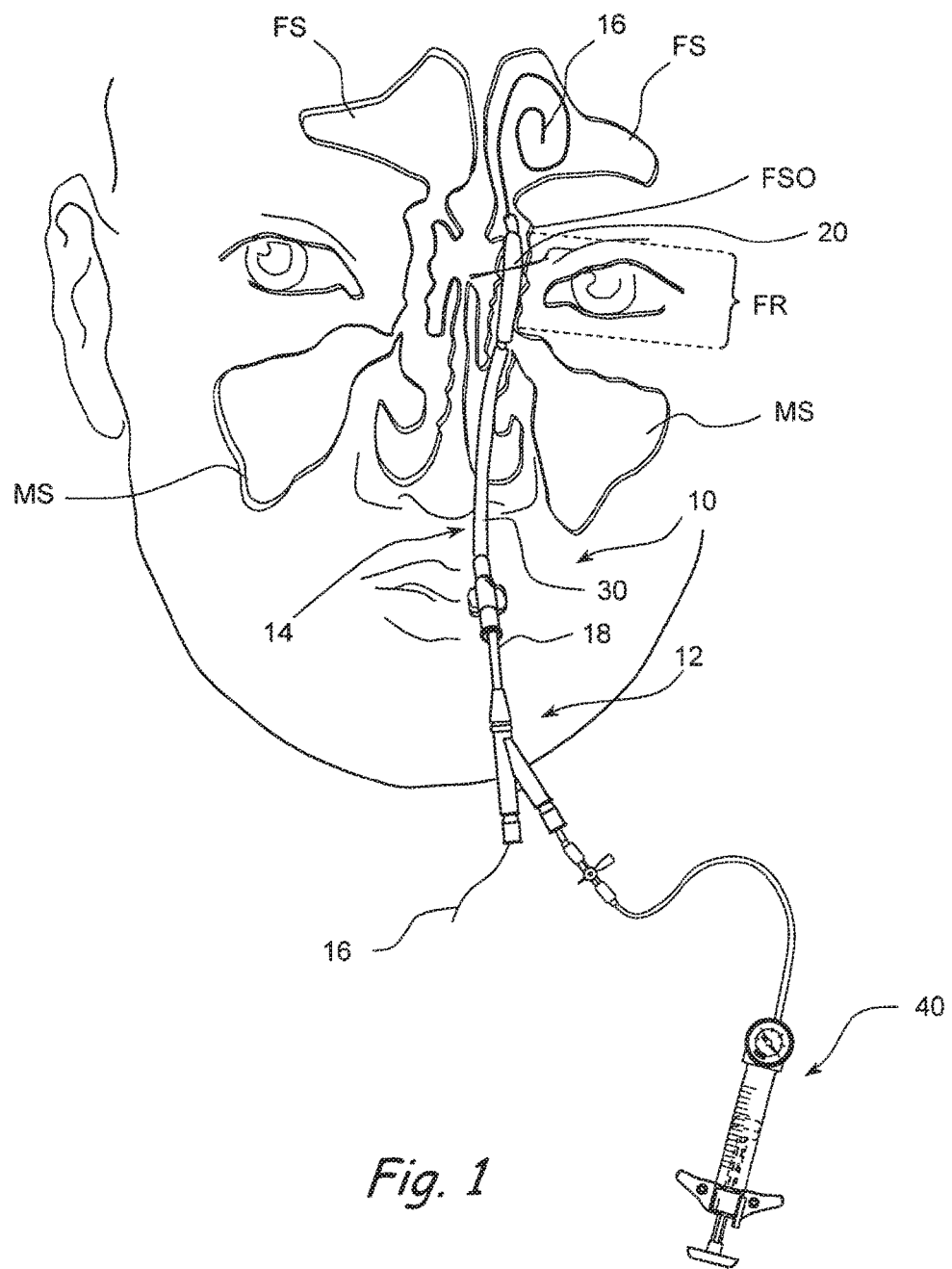
FIG. 1 is a diagram of the paranasal anatomy of a human head wherein a dilation catheter system of the present invention has been inserted and is being used to simultaneously dilate the frontal sinus ostium and adjacent frontal recess.

The following detailed description, the accompanying drawings and the above-set-forth Brief Description of the Drawings are intended to describe some, but not necessarily all, examples or embodiments of the invention. The contents of this detailed description do not limit the scope of the invention in any way.

A number of the drawings in this patent application show anatomical structures of the ear, nose and throat. In general, these anatomical structures are labeled with the following reference letters:

| | |
|---|---|
| Nasal Cavity | NC |
| Nasopharynx | NP |
| Frontal Sinus | FS |
| Frontal Sinus Ostium | FSO |
| Frontal Recess | FR |
| Ethmoid Air Cells | EAC |
| Intersinus Septum | ISS |
| Sphenoid Sinus | SS |
| Sphenoid Sinus Ostium | SSO |
| Maxillary Sinus | MS |

The term "diagnostic or therapeutic substance" as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or nan-fluid. For example, in some applications where it is desired to treat or prevent a microbial infection, the substance delivered may comprise pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents of modifies an allergic response (e.g., an antihistamine, cytokine inhibitor, leucotriene inhibitor, IgE inhibitor, immunomodulator), etc. Other non-limiting examples of diagnostic or therapeutic substances that may be useable in this invention are described in copending U.S. patent application Ser. No. 10/912,578 entitled Implantable Devices and Methods for Delivering Drugs and Other Substances to Treat Sinusitis and Other Disorders filed on Aug. 4, 2004, now U.S. Pat. No. 7,361,168, issued on Apr. 22, 2008, the entire disclosure of which is expressly incorporated herein by reference.

The term "frontal recess" means the natural or surgically altered opening or passageway extending from an ostium or opening in a frontal sinus into the nasal cavity.

The term "frontal outflow tract" or the acronym "FOT" means an ostium or opening in a frontal sinus along with any frontal recess that extends from that ostium or opening to the nasal cavity.

Each of the terms "ostium," "opening of a paranasal sinus" or "opening in a paranasal sinus" as used herein shall mean any accessible opening in a paranasal sinus or craniafacial air cell, including but not limited to; natural ostia, surgically or medically altered ostia, surgically created or man-made openings, gastrostomy openings, ostiotomy openings, trephination openings, burr holes, drilled holes, ethmoidectomy openings, anatomical passageways, natural or man made passages, etc., unless otherwise specified.

The term "working length" as used herein with respect to balloons or other dilators shall mean the length of that portion of the balloon or other dilator that actually contacts and dilates tissue. For example, in the case of a balloon that, when inflated, has a cylindrical midregion that contacts and dilates adjacent tissue and tapered end regions that do not contact and dilate adjacent tissue, the working length of such balloon is the length of the cylindrical midregion that contacts and dilates adjacent tissue.

Optionally, any of the working devices and guide catheters described herein may be configured or equipped to receive or be advanced over a guidewire or other guide member (e.g., an elongate probe, strand of suture material, other elongate member) unless to do so would render the device inoperable for its intended purpose. Some of the specific examples described herein include guidewires, but it is to be appreciated that the use of guidewires and the incorporation of guidewire lumens is not limited to only the specific examples in which guidewires or guidewire lumens are shown. The guidewires used in this invention may be constructed and coated as is common in the art of cardiology, but may be substantially shorter than those used in cardiology applications. This may include the use of coils, tapered or non-tapered core wires, radiopaque tips and/or entire lengths, shaping ribbons, variations of stiffness, PTFE, silicone, hydrophilic coatings, polymer coatings, etc. For the scope of this invention, these wires may possess dimensions of length between 5 and 120 cm and outer diameter between 0.005" and 0.050". In embodiments of the invention where an elongate guide member (e.g., a guidewire) of a substantially fixed shape is specified, such may be accomplished by utilizing a guide member (e.g., guidewire) that is fully or partially formed of rigid or malleable material and is pre-shaped to a desired substantially fixed configuration (e.g., a desired curve near its distal end) prior to insertion into the subject's body.

It is to be appreciated that various modalities can be used with the devices and methods disclosed herein for navigation and imaging of the devices within the anatomy. For example, the devices disclosed herein may comprise an endoscope for visualization of the target anatomy. The devices may also comprise ultrasound imaging modalities to image the anatomical passageways and other anatomical structures. The devices disclosed herein may comprise one or more magnetic elements especially on the distal end of the devices. Such magnetic elements may be used to navigate through the anatomy by using external magnetic fields. Such navigation may be controlled digitally using a computer interface. The devices disclosed herein may also comprise one or more markers (e.g. infra-red markers). The markers can be used to track the precise position and orientation of the devices using image guidance techniques. Several other imaging or navigating modalities including but not limited to fluoroscopic, radiofrequency localization, electromagnetic, magnetic and other radiative energy based modalities may also be used with the methods and devices disclosed herein. These imaging and navigation technologies may also be referenced by computer directly or indirectly to pre-existing or simultaneously created 3-D or 2-D data sets which help the doctor place the devices within the appropriate region of the anatomy. Examples of specific navigation apparatus and methods that may be used in conjunction with the devices and methods of this invention include but are not limited to those described in co-pending U.S. patent application Ser. No. 11/037,548 entitled "Devices, Systems and Methods For Treating Disorders of the Ear, Nose and Throat," now U.S. Pat. No. 7,462,175, issued on Dec. 9, 2008, which is expressly incorporated herein by reference.

Also, as described more fully hereblow, the devices of the present invention may include visible markers that may be viewed directly or endoscopically to facilitate the desired positioning of the devices within the body.

Figure 2:
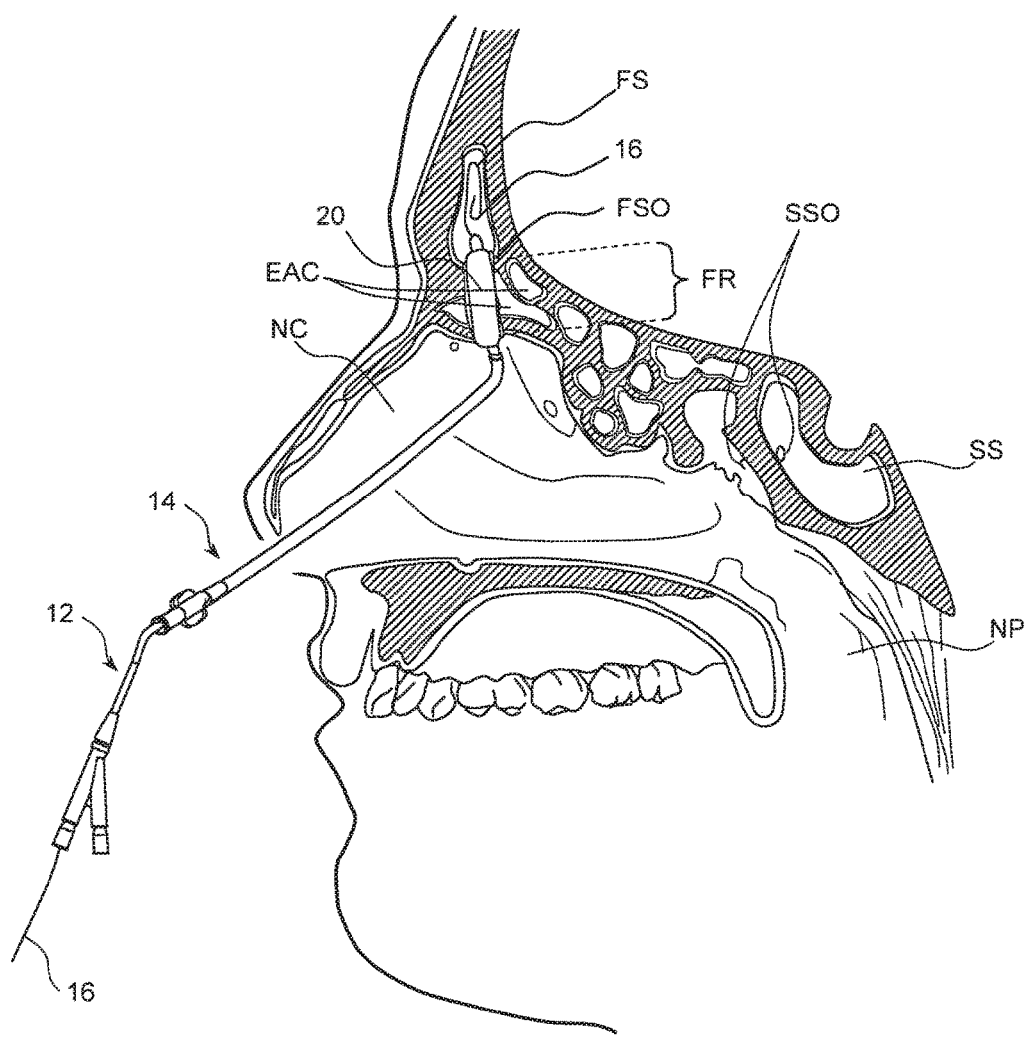
FIG. 2 is a sagital sectional view through the right nasal cavity wherein a dilation catheter system of the present invention has been inserted and is being used to simultaneously dilate the frontal sinus ostium and adjacent frontal recess.
Figure 4:
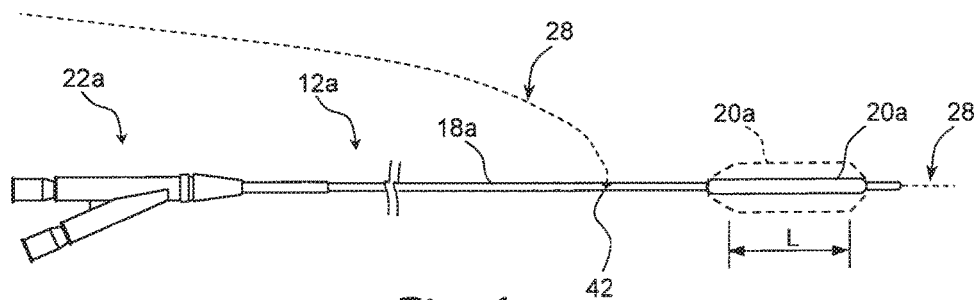
FIG. 4 is a broken, side elevational view of a rapid exchange embodiment of a dilation catheter device of the present invention.

FIGS. 1-2 show the use of an embodiment of a dilation catheter system 10 to simultaneously dilate a frontal sinus ostium FSO and adjacent frontal recess FR in a human subject. Frontal recess anatomy has heretofore been generally taught as having an hour glass shape so it was believed that a relatively short dilator (such as a balloon) was all that was needed to dilate most frontal sinus anatomy. Unexpectedly, however, Applicants have discovered that in a fairly large population of patients there are actually multiple constrictions along the frontal recess. As a result, Applicants developed the present invention. In general, the embodiment of the dilation catheter system 10 shown in the drawings comprises a dilation catheter 12, a tubular guide 14 and a guidewire 16. These components of the system 10 are shown in greater detail in FIG. 4.

Generally, at least one of the tubular guide 14 and/or the guidewire 16 will have a predetermined (e.g., substantially fixed) shape (e.g., having a fixed curve near its distal end) prior to its insertion into the body. This fixed shape facilitates easy insertion of the guidewire 16 and/or tubular guide 14 into the frontal recess or other desired location within the nasal cavity or paranasal sinus anatomy. In some instances, one or both of the guidewire 16 and/or tubular guide 14 will be of generally rigid construction and manufactured in the desired predetermined or substantially fixed shape. In other instances, all or a portion of the guidewire 16 and/or tubular guide 14 may be of malleable construction such that the surgeon may bend or pre-form that guidewire 16 or tubular guide 14 to the desired shape prior to its insertion into the subject's body.

In the particular example shown in the drawings and discussed herebelow, the tubular guide 14 is generally rigid and has a substantially fixed shape. The guidewire 16 is substantially flexible and use of the guidewire is optional. It is to be appreciated, however, that in other embodiments the guidewire 16 may be more rigid and of substantially fixed shape and use of the tubular guide 16 may be optional.

Figure 3A:
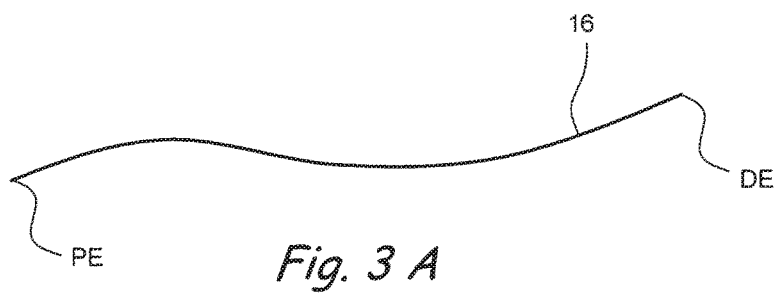
FIGS. 3A-3C are side views of devices that comprise one embodiment of a dilation catheter system of the present invention.

In this example, the guidewire 16, seen in FIG. 3A, is a flexible sinus guidewire with a soft tip, a length of 100 cm and a diameter of 0.035 inch. This guidewire is commercially available under the name Relieve™ Sinus Guidewire from Acclarent, Inc., Menlo Park, Calif. It will be appreciated, however, that other guidewires and other sizes of guidewires may alternatively be used.

Figure 3B:
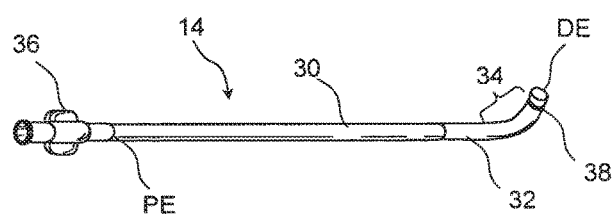

Also, in this example, the tubular guide 14 as seen in FIG. 3B, comprises a semi-flexible tube with a malleable proximal shaft 30 and a plastic distal portion 32 having a curve 34 formed near its distal end DE. A radiopaque marker 38 is mounted near the distal end DE of this tubular guide 14. This tubular guide is available commercially under the name Relieva™ Sinus Guide Catheter from Acclarent, Inc. of Menlo Park, Calif. This tubular guide 14 is available with a range of curves 32 (i.e., 0°, 30°, 70°, 90° and 110°. Typically, for frontal sinus procedures such as that described herein a curve of 70° is most suitable. It will be appreciated, however, that other guidewires and other sizes of guidewires may alternatively be used.

Figure 3C:
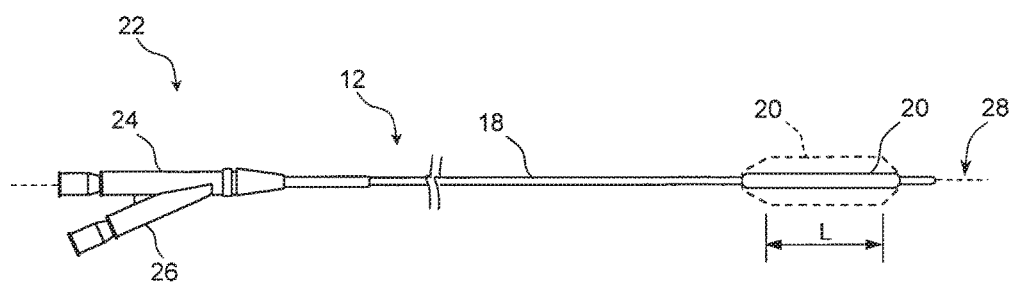

The dilation catheter 12 of this example, as seen in detail in FIG. 3C, comprises an elongate catheter body 18 having a proximal end PE and a distal end DE. An elongate balloon 20 is mounted on the catheter body 18 at a location near its distal end DE. This balloon 20 has a working length L that is specifically sized to extend from the frontal sinus ostium FSO through substantially all of the frontal recess FR, thus rendering this balloon 20 capable of dilating substantially the entire frontal outflow tract (i.e., the frontal sinus ostium and all or nearly all of the adjacent frontal recess), without the need for repeated inflations of the balloon 20 with longitudinal repositioning of the catheter between inflations. In this regard, although it may be deemed appropriate to repeat inflation of the balloon 20 more than one time to dilate the frontal sinus ostium FSO and adjacent frontal recess FR, no longitudinal repositioning of the catheter body 18 will be required between such inflations. This dilation catheter 12 is available commercially under the name Relieva™ Sinus Balloon Catheter from Acclarent, Inc., Menlo Park, Calif. A fixed guidewire 28 may optionally extend from the distal end of the dilation catheter 12, as seen in FIG. 3C. Such fixed guidewire 28 may allow the dilation catheter 12 to be used without a separate guidewire 16.

The actual working length L and diameter of the balloon 20 may vary depending on the anatomy, age and/or size of the subject. The working length of the balloon can be between about 12 mm and 30 mm. For example, the following table sets forth a nonlimiting example different balloon sizes that may be provided for treatment of frontal sinusitis in subjects of normal body size and weight ranging in age from childhood to adulthood.

| Typical Patient Age Range | Dilator (e.g., Balloon) Width (Fully Expanded) | Dilator (e.g., Balloon) Working Length |
| --- | --- | --- |
| >17 | about 5 mm to about 7 mm | about 24 mm |
| 14-17 | About 4 mm to about 7 mm | About 21 mm |
| 10-14 | About 3 mm to about 6 mm | About 18 mm |
| 6-10 | About 2 mm to about 5 mm | About 15 mm |
| <6 | About 2 mm to about 4 mm | About 12 mm |

Applicant's current data suggests that a balloon 20 having a working length of about 24 mm and a fully expanded width of about 5 mm to about 7 mm may be used to expand the frontal sinus ostium FSO as well as substantially all of the adjacent frontal recess FR in most adult or fully grown humans without the need for repeated inflations of the balloon 20 or without longitudinal repositioning of the catheter between inflations.

The procedure by which the devices are inserted and used may vary somewhat from surgeon to surgeon and/or from case to case. One particular, non-limiting example of such a procedure is described herebelow with reference to the showings of FIGS. 1 and 2.

During performance of this procedure, an endoscope, such as a Karl Storz Hopkins II 4 mm scope with a 70 degree viewing angle may optionally be inserted into the nose and used, alone or in combination with other imaging techniques, to view the advancement and positioning of devices during the procedure in accordance with known practice or as described in U.S. patent application Ser. Nos. 10/829,917, now U.S. Pat. No. 7,654,997, issued on Feb. 2, 2010; 10/944,270, published as U.S. Pub. No. 2006/0004323 on Jan. 5, 2006; 11/037,548, now U.S. Pat. No. 7,462,175, issued on Dec. 9, 2008,; 11/193,020, now U.S. Pub. No. 2006/0063973, published on Mar. 23, 2006; 11/150,847, now U.S. Pat. No. 7,803,150, issued on Sep. 28, 2010; 11/116,118, now U.S. Pat. No. 7,720,521, issued on May 18, 2010, each of which is expressly incorporated herein by reference. Alternatively or additionally, radiographic imaging (e.g., C-arm fluoroscopy) may be used to view the positioning and guide the placement of devices during the procedure in accordance with known practice or as described in U.S. patent application Ser. Nos. 10/829,917, now U.S. Pat. No. 7,654,997, issued on Feb. 2, 2010; 10/944,270, published as U.S. Pub. No. 2006/0004323 on Jan. 5, 2006; 11/037,548, now U.S. Pat. No. 7,462,175, issued on Dec. 9, 2008,; 11/193,020, now U.S. Pub. No. 2006/0063973, published on Mar. 23, 2006; 11/150,847, now U.S. Pat. No. 7,803,150, issued on Sep. 28, 2010; 11/116,118, now U.S. Pat. No. 7,720,521, issued on May 18, 2010, each of which is expressly incorporated herein by reference. Also, alternatively or additionally, the devices used in this procedure may be equipped with sensors and image guidance technology may be used to view the positioning and guide the placement of devices during the procedure in accordance with known practice or as described in U.S. patent application Ser. No. 11/116,118, now U.S. Pat. No. 7,720,521, issued on May 18, 2010, which is expressly incorporated herein by reference.

In this example, the guidewire 16 may be initially introduced, distal end first, into the lumen of the tubular guide 14. Thereafter, the tubular guide 14 (with the guidewire 16 inserted therein) is inserted through the subject's nostril with the curve 32 of the tubular guide 14 pointing upwardly. The distal end DE of the tubular guide 14 is maneuvered through the middle meatus to a position where its distal end DE is adjacent to and in alignment with the frontal recess FR. The guidewire 16 is then advanced out of the open distal end DE of the tubular guide 14, through the frontal recess FR, through the frontal sinus ostium FSO and into the frontal sinus FS. In some cases, it may be desirable to push a length of the guidewire into the frontal sinus FS such that it becomes coiled within the sinus cavity as seen in FIGS. 1 and 2. This tends to deter inadvertent slippage of the guidewire 16 out of position and the coiled guidewire 16 within the frontal sinus FS may be viewed by radiographic means to verify that the FOT has been successfully wired.

It is to be appreciated that, although the dilation catheter 12 shown in FIGS. 1-2 and 3C is an over-the-wire type device that has a guidewire lumen that extends from one end of the catheter to the other, various other guidewire lumen configurations and/or fixed guidewire tips may be employed instead. For example, a guidewire may be affixed to and extend distally from the distal end of the catheter body 18. Or, as shown in the alternative example of FIG. 4, a rapid exchange embodiment of the dilation catheter 12a may be utilized. This rapid exchange embodiment of the dilation catheter 12a comprises a catheter body 18a having a proximal hub 22a on its proximal end and a guidewire lumen that extends from a side port 42 located between the proximal and distal ends of the catheter body 18a though an opening in the distal end of the catheter body 18a. In this manner, the guidewire 28 will extend through only a distal portion of the catheter body 18a and the proximal portion of the guidewire will be outside of the catheter body 18a as shown.

It is to be further appreciated that, in at least some embodiments, substances (e.g., therapeutic or diagnostic substances, radiographic contrast medium, medicaments, lavage fluid, etc.) may be injected through a lumen of the catheter body 18. In some embodiments, the guidewire 28 may be smaller in diameter than the guidewire lumen such that substances may be injected through the guidewire lumen even while the guidewire is positioned therein.

Thereafter, the proximal end PE of the guidewire 16 is inserted into the distal opening of a guidewire lumen that extends through the dilation catheter 12 and the dilation catheter 12 is advanced over the guidewire 16 and through the lumen of the tubular guide 14 to a position where the balloon 20 occupies the frontal sinus ostium FSO and substantially all or all of the adjacent frontal recess FR. An inflator device (e.g., the Relieva™ Sinus Balloon Inflation Device, Aclarent, Inc., Menlo Park, Calif.) is then connected to the inflation sidearm 26 of the dilation catheter's proximal hub 22 and is used to inflate the balloon 20 to its expanded configuration. Typically, in applications where the balloon 20 is used to dilate the frontal sinus ostium FSO and adjacent frontal recess FR, this balloon will be inflated to a pressure of approximately 4-12 ATM. The balloon 20 may reach its nominal (target) diameter at an inflation pressure of approximately 4-8 ATM. This inflation may be repeated one or more times at the discretion of the surgeon, but no repositioning of the balloon 20 is required between successive inflations. In this manner, the frontal sinus ostium FSO and frontal recess FR are dilated, thereby improving patency of the FOT and facilitating drainage from and healing of the diseased frontal sinus FS.

Figure 5:
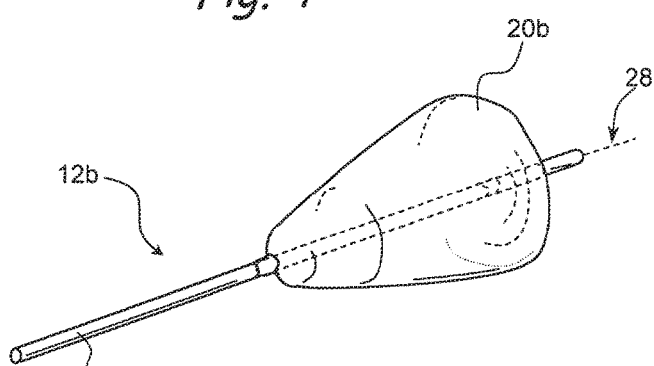
FIG. 5 is a partial perspective view of an embodiment of a dilation catheter device of the present invention having a tapered dilation balloon.

If the working length L of the balloon 20 is longer than the length of the frontal sinus ostium FSO and adjacent frontal recess FR, a proximal portion of the balloon may be permitted to remain within the distal end of the tubular guide 14 or another suitable sheath or constraining structure such that only a portion of the balloon 20 becomes inflated. This essentially provides a balloon 20 of adjustable length. Alternatively or additionally, the diameter of the balloon 20 may also vary over its length. For example, a 24 mm long balloon 20 may have a first region (e.g., 16 mm) which inflates to a first diameter (e.g., 7 mm) and a second region that inflates to a second diameter (e.g., 5 mm). In another example, shown in FIG. 5, a dilation catheter 12b may comprise a catheter body 18b having a balloon 20b mounted thereon, such balloon 20b being may be continuously tapered such that one end of the balloon 20b inflates to a first diameter and the other end of the balloon 20b inflates to a smaller second diameter, with a continuous diametric taper therebetween.

Figures 6A, 6B:
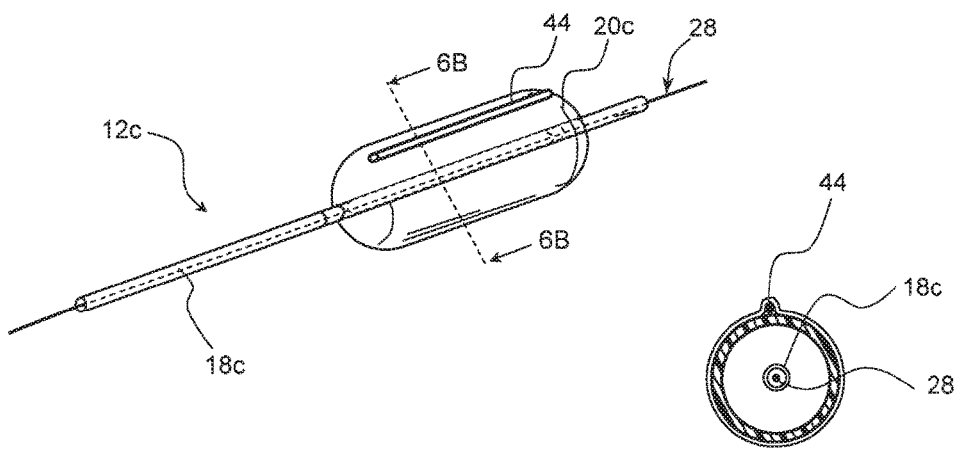
FIG. 6A is a partial perspective view of an embodiment of a dilation catheter device of the present invention having a dilation balloon that incorporates a force concentrating member.
FIG. 6B is a cross sectional view through line 6B-6B of FIG. 6A.

Also, alternatively or additionally, as shown in FIGS. 6A and 6B, an embodiment the dilation catheter 12c may comprise a catheter body 18c having a balloon 20c mounted thereon, wherein such balloon 20c incorporates one or more force concentrating members 44 (such as longitudinal wires embedded in the wall of the balloon 20c) or other surface protrusion(s) that concentrate the dilatory force of the balloon in specific area(s) rather than allowing the balloon 20c to exert the same outwardly directed dilatory force about its entire diameter.

Various other balloon shapes and balloon constructions may be incorporated in the dilation catheters 12, 12a, 12b or 12c including those described in the parent patent applications of which this application is a continuation-in-part. Some particular nonlimiting examples of such shapes and/or constructions include the following:

The balloon or other dilator may additionally be constructed to deliver diagnostic or therapeutic substances to adjacent tissues, such as through pores, coatings, micro-penetrating members, etc.

The balloon material may be of varying thickness along the length of the balloon to enhance folding or to permit it to expand in an intentionally non-uniform fashion.

To prevent "winging" the balloon may be preshaped with set 'hinge' areas that naturally fold when the balloon is deflated—these hinge areas may run longitudinally along the balloon or may be helically located.

The catheter shaft extending through the balloon may be longitudinally moved by the operator to lengthen or shorten the balloon length to adjust to different anatomies.

The distal tip of the balloon may be curved to facilitate placement and also to orient the tip away from the skull base.

As seen in FIG. 2, The medial wall of the orbit (specifically the lamina papyracea) is reinforced by ethmoid air cells that form a "honeycomb" structure between the medial wall of the orbit and the frontal recess FR. In at least some applications of the present invention, dilation of the frontal recess FR causes bone to become cracked, fractured, rearranged or repositioned and, in at least some cases, results in compression or remodeling of one or more ethmoid air cells EAC.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless to do so would render the embodiment or example unsuitable for its intended use. Also, where the steps of a method or process are described, listed or claimed in a particular order, such steps may be performed in any other order unless to do so would render the embodiment or example not novel, obvious to a person of ordinary skill in the relevant art or unsuitable for its intended use. All reasonable additions, deletions, modifications and alterations are to be considered equivalents of the described examples and embodiments and are to be included within the scope of the following claims.

What is claimed is:

1. A method for dilating a frontal sinus ostium in a human or animal subject with a dilation catheter, the dilation catheter comprising a catheter shaft, a dilator positioned along a distal portion of the catheter shaft and having a sufficient length to extend through the frontal sinus ostium, the method comprising:
 (a) inserting a guide into a head of the subject;
 (b) advancing the guide to the frontal sinus ostium, then stopping advancement of the guide when a distal portion of the guide is positioned within or adjacent to the frontal sinus ostium;
 (c) advancing the dilation catheter relative to the guide to position the dilator within the frontal sinus ostium; and
 (d) expanding the dilator, wherein expansion of the dilator results in dilation of the frontal sinus ostium and at least some breakage of bone adjacent to the frontal sinus ostium.

2. The method according to claim 1, wherein the dilation catheter further comprises a guidewire lumen extending from an open proximal end of the catheter shaft to an open distal end of the catheter shaft, and the method further comprises:

(a) inserting a guidewire into the head of the subject; and
(b) advancing the dilator over the guidewire via the guidewire lumen of the dilation catheter.

3. The method according to claim 1, wherein the dilation of the frontal sinus ostium results in at least some breakage or movement of bone adjacent to the frontal sinus ostium.

4. The method according to claim 1, wherein the step of expanding the dilator is performed without removal, cutting, or ablation of tissue.

5. The method according to claim 1, further comprising the step of removing, cutting, or ablating tissue within the head of the subject.

6. The method according to claim 1, wherein inserting the guide into the head of the patient further comprises inserting the guide into a nostril of the patient.

7. The method according to claim 1, further comprising the step of retracting the guide relative to the dilation catheter prior to expansion of the dilator.

8. The method according to claim 1, further comprising the step of inserting an endoscope into the head of the patient.

9. The method according to claim 1, further comprising the step of placing a therapeutic or diagnostic substance delivering implant within the frontal sinus ostium or frontal sinus.

10. The method according to claim 1, further comprising bending at least the distal portion of the guide to a curved shape prior to insertion in the patient's head, wherein the curved shape is substantially retained during use.

11. The method according to claim 10, wherein the step of bending occurs at the time of manufacture, wherein the guide is sufficiently rigid to maintain the curved shape until and during use.

12. The method according to claim 1, wherein the distal portion of the guide comprises a curve, wherein at least a portion of the dilation catheter is flexible to allow the dilation catheter to traverse the curve while advancing the dilation catheter relative to the guide.

13. The method according to claim 1, wherein the method is performed in combination with a functional endoscopic sinus surgery procedure.

14. The method according to claim 1, wherein expanding the dilator further comprises expanding the dilator to an expanded configuration, wherein a cross-sectional dimension of the expanded configuration is between approximately 3 mm and approximately 7 mm.

15. The method according to claim 1, wherein the dilator includes a length of approximately 12 mm to approximately 24 mm.

16. A method for dilating a frontal sinus ostium in a human or animal subject with a dilation catheter, the dilation catheter comprising a catheter shaft and a dilator positioned along a distal portion of the catheter shaft, the method comprising:

(a) inserting a guide into a head of the subject;
(b) advancing the guide into the frontal sinus ostium;
(c) advancing the dilation catheter relative to the guide to position the dilator within the frontal sinus ostium while the dilator is in a collapsed configuration;
(d) expanding the dilator to an expanded configuration while the dilator is positioned within the frontal sinus ostium; and
(e) dilating the frontal sinus ostium, wherein the act of dilating the frontal sinus ostium comprises breaking bone adjacent to the frontal sinus ostium.

17. The method according to claim 16, further comprising bending at least a distal portion of the guide to a curved shape having a bend angle prior to insertion in the head of the subject.

18. The method according to claim 17, wherein the step of bending occurs at the time of manufacture, wherein the guide is sufficiently rigid to maintain the curved shape until and during use.

19. The method according to claim 16, further comprising removing, cutting, or ablating tissue within the head of the subject.

20. A method for dilating a frontal sinus ostium in a human or animal subject with a dilation catheter, the dilation catheter comprising a catheter shaft, a dilator positioned along a distal portion of the catheter shaft, the method comprising:

(a) inserting the guide into a head of the subject;
(b) advancing the guide into the frontal sinus ostium;
(c) advancing the dilation catheter relative to the guide to position the dilator within the frontal sinus ostium; and
(d) expanding the dilator to break bone adjacent to the frontal sinus ostium, thereby dilating the frontal sinus ostium.

* * * * *